United States Patent
Nam et al.

(10) Patent No.: US 7,319,010 B2
(45) Date of Patent: Jan. 15, 2008

(54) DETECTION AND TREATMENT OF CANCERS OF THE COLON

(75) Inventors: Myeong Nam, Seoul (KR); Juan Madoz-Gurpide, Madrid (ES); Hong Wang, Edmonds, WA (US); David E. Misek, Ann Arbor, MI (US); Samir M. Hanash, Mercer Island, WA (US)

(73) Assignee: The Regents of the University of Michigan, Ann Arbor, MI (US)

( * ) Notice: Subject to any disclaimer, the term of this patent is extended or adjusted under 35 U.S.C. 154(b) by 426 days.

(21) Appl. No.: 10/844,216

(22) Filed: May 12, 2004

(65) Prior Publication Data

US 2005/0079560 A1  Apr. 14, 2005

Related U.S. Application Data

(60) Provisional application No. 60/469,717, filed on May 12, 2003.

(51) Int. Cl.
*G01N 33/53* (2006.01)
*C07K 1/00* (2006.01)
*C07K 16/00* (2006.01)

(52) U.S. Cl. .................... 435/7.1; 530/350; 530/387.1

(58) Field of Classification Search ..................... None
See application file for complete search history.

(56) References Cited

FOREIGN PATENT DOCUMENTS

WO    WO 99/10567    1/1999

OTHER PUBLICATIONS

Taber's Cyclopedic Medical Dictionary (1985, F.A. Davis Company, Philadelphia, p. 274).*
Krontiris and Capizzi (Internal Medicine, 4th Edition, Editor-in-chief Jay Stein, Elsevier Science, 1994 Chapters 71-72, pp. 699-729).*
Greenbaum et al. (Genome Biology, 2003, vol. 4, Issue 9, pp. 117.1-117.8).*
Brennan et al. (J. Autoimmunity, 1989, 2 (suppl.): 177-186).*
Zimmer (Cell Motility and the Cytoskeleton, 1991. 20:325-337).*
Hell et al. (Laboratory Investigation, 1995, 73: 492-496).*
Fu et al. (EMBO J., 1996, 15:4392-4401).*
Vallejo et al. (Biochimie, 2000 82:1129-1133).*
Jang et al. (Clinical Exp. Metastasis, 1997, 15: 469-483).*
Busken, C et al, (Digestive Disease Week Abstracts and Itinerary Planner, 2003, abstract No. 850).*
Stocket et al., "A survey of the humoral immune response of cancer patients to a panel of human tumor antigens," J. Exp. Med., 187:1349 [1998].
Boon and Old, "Cancer Tumor antigens," Curr. Opin. Immunol. 9:681 [1997].
Soussl, "p53 Antibodies in the sera of patients with various types of cancer: a review," Cancer Res. 60:1777 [2000].
Brichory et al., "Proteomics-based identification of protein gene product 9.5 as a tumor antigen that induces a humoral immune response in lung cancer," Cancer Research 61, 7908-7912 [2001]).
Old and Chen, "New Paths in Human Cancer Serology," J. Exp. Med. 187:1163 [1998].
Hibi et al., "PGP9.5 as a candidate tumor marker for non-small-cell lung cancer," American Journal of Pathology 155, 711-715 [1999].
Kurihara et al., "Loss of Uch-L1 and Uch-L3 leads to neurodegeneration, posterior paralysis and dysphagia," Human Molecular Genetics 10, 1963-1970 [2001].
Tezel et al., "PGP9.5 as a prognostic factor in pancreatic cancer," Clinical Cancer Research 6, 4764-4767 [2000].
Wada et al., "Cleavage of the C-terminus of NEDD8 by UCH-L3," Biochem. Biophys. Res. Commun. 251,688-692 [1998].
Proteomics, "Molecular profiling of the immune response in colon cancer using protein microarrays: occurance of autoantibodies to ubiquitin C-terminal hydrolase L3," Nov. 2003;3(11):2108-15.
Giordano et al., "Organ-specific molecular classification of primary lung, colon, and ovarian adenocarcinomas using gene expression profiles," American Journal of Pathology 159, 1231-1238 [2001].
Schwartz et al., "Gene expression in ovarian cancer reflects both morphology and biological behavior, distinguishing clear cell from other poor-prognosis ovarian carcinomas," Cancer Research 62, 4722-4729 [20.

* cited by examiner

*Primary Examiner*—Susan Ungar
*Assistant Examiner*—Peter J. Reddig
(74) *Attorney, Agent, or Firm*—Casimir Jones, S.C.

(57) ABSTRACT

The present invention relates to compositions and methods for cancer therapies and diagnostics, including but not limited to, cancer markers. In particular, the present invention provides tumor antigens associated with specific cancers and diagnostic assays for the detection of such antigens and associated autoantibodies as indicative of the presence of specific cancers. The present invention further provides cancer immunotherapy utilizing the tumor antigens of the present invention.

2 Claims, No Drawings

DETECTION AND TREATMENT OF CANCERS OF THE COLON

This application claims priority to provisional patent application Ser. No. 60/469,717, filed May 12, 2003, which is herein incorporated by reference in its entirety.

This invention was made in part with government support under Grant No. CA084953 awarded by the National Cancer Institute. The Government has certain rights in the invention.

FIELD OF THE INVENTION

The present invention relates to compositions and methods for cancer therapies and diagnostics, including but not limited to, cancer markers. In particular, the present invention provides tumor antigens associated with specific cancers and diagnostic assays for the detection of such antigens and associated autoantibodies as indicative of the presence of specific cancers.

BACKGROUND OF THE INVENTION

The term cancer collectively refers to more than 100 different diseases that affect nearly every part of the body. Throughout life, healthy cells in the body divide, grow, and replace themselves in a controlled fashion. Cancer starts when the genes directing this cellular division malfunction, and cells begin to multiply and grow out of control. A mass or clump of these abnormal cells is called a tumor. Not all tumors are cancerous. Benign tumors, such as moles, stop growing and do not spread to other parts of the body. But cancerous, or malignant, tumors continue to grow, crowding out healthy cells, interfering with body functions, and drawing nutrients away from body tissues. Malignant tumors can spread to other parts of the body through a process called metastasis. Cells from the original tumor break off, travel through the blood or lymphatic vessels or within the chest, abdomen or pelvis, depending on the tumor, and eventually form new tumors elsewhere in the body.

Only 5-10% of cancers are thought to be hereditary. The rest of the time, the genetic mutation that leads to the disease is brought on by other factors. The most common cancers are linked to smoking, sun exposure, and diet. These factors, combined with age, family history, and overall health, contribute to an individual's cancer risk.

Several diagnostic tests are used to rule out or confirm cancer. For many cancers, the most definitive way to do this is to take a small sample of the suspect tissue and look at it under a microscope—this process is called a biopsy. However, many biopsies are invasive, unpleasant procedures with their own associated risks, such as pain, bleeding, infection, and tissue or organ damage. In addition, if a biopsy does not result in an accurate or large enough sample, a false negative or misdiagnosis can result, often required that the biopsy be repeated. What is needed in the art are improved methods to specifically detect, characterize, and monitor specific types of cancer.

SUMMARY OF THE INVENTION

The present invention relates to compositions and methods for cancer therapies and diagnostics, including but not limited to, cancer markers. In particular, the present invention provides tumor antigens associated with specific cancers and diagnostic assays for the detection of such antigens and associated autoantibodies as indicative of the presence of specific cancers.

There is increasing evidence for an immune response to cancer in humans, demonstrated by the identification of autoantibodies to tumor antigens (Stocket et al., J. Exp. Med., 187:1349 [1998]; Boon and Old, Curr. Opin. Immunol. 9:681 [1997]; Soussl, Cancer Res. 60:1777 [2000]; Old and Chen, J. Exp. Med. 187:1163 [1998]). The identification of panels of tumor antigens that elicit a humoral response has utility in cancer screening, diagnosis, and in establishing a prognosis. Such antigens also have utility in immunotherapy against cancers. Several approaches are currently available for the identification of tumor antigens. The present invention provides a proteomic-based approach for the identification of tumor antigens that induce an antibody response. In contrast to other approaches based on the analysis of recombinant proteins, a proteomic approach allows identification of autoantibodies to proteins that are directly derived from cancer cells or tumors and thus may uncover antigenicity associated with post-translational modification.

To date, discovery of autoantibodies has been limited by the detection technology. In some embodiments, the present invention provides a combination of liquid-phase protein separation and protein microarray technology that provides an effective means to array a wide repertoire of tumor cell proteins derived from the tumor type of interest. As a result, detection of specific interactions between tumor cell antigens in individual fractions and antibodies in patient sera is substantially facilitated. Experiments conducted during the course of development of the present invention comprising hybridization of these protein microarrays with sera from cancer patients and controls resulted in the detection of a fraction (L04428) that exhibited a high frequency of immunoreactivity with colon cancer sera. This fraction was analyzed by Q-TOF tandem mass spectrometry, and was found to contain UCH-L3. Subsequent independent analysis by means of 2-D PAGE and Western blotting uncovered autoantibodies against UCH-L3 in sera from 19/43 newly diagnosed patients with colon cancer. However, no antibodies were detected in sera obtained from 15 healthy individuals, 15 patients with colon adenomas, and 24 patients with lung cancer.

Another member of the UCHL family, UCH-L1, was previously identified as an antigen that induces an antibody response in lung cancer (Brichory et al., Cancer Research 61, 7908-7912 [2001]). UCH-L1 is widely expressed in neuronal tissues at all stages of neuronal differentiation, and may be expressed during neuroendocrine differentiation of lung cancer. Ubiquitination and targeting of cellular proteins for subsequent degradation via ubiquitin-mediated proteolysis is an important mechanism regulating a broad spectrum of cellular processes. In tumors, increased deubiquitination of cyclins by UCH-L1 may contribute to the uncontrolled growth of somatic cells (Hibi et al., American Journal of Pathology 155, 711-715 [1999]; Kurihara et al., Human Molecular Genetics 10, 1963-1970 [2001]; Tezel et al., Clinical Cancer Research 6, 4764-4767 [2000]).

The methods of the present invention allow protein microarray screening of patient sera to determine reactivity with individual protein fractions. A humoral response directed against UCH-L3, detectable in both the LoVo colon adenocarcinoma cell line and in colon tumors, occurred in 44% of newly diagnosed patients with colon adenocarcinoma. DNA microarray analysis revealed that UCH-L3 was expressed at approximately 3-5 fold higher levels in colon tumors than that observed in all other tumor types examined. These findings are in contrast to normal expression of UCH-L3, whose mRNA is highly enriched in heart, skeletal muscle and testis (Wada et al., Biochem. Biophys. Res. Commun. 251,688-692 [1998]), but much lower in all other tissues, thus demonstrating aberrant expression of UCH-L3 in colon cancer. Accordingly, in some embodiments, the present invention provides methods of detecting autoantibodies to the UCH-L3 as a biomarker for colon cancer.

In other embodiments, UCH-L3 expression is analyzed. In yet other embodiments, the existence of one or more other markers is determined to characterize the presence, absence, or stage of colon cancer in a subject. For example, in some embodiments, the present invention provides a method for detecting cancer, comprising providing a sample from a subject suspected of having cancer; and detecting the presence of UCH-L3 in the sample, thereby detecting cancer. In some embodiments, the cancer is colorectal cancer. In some embodiments, the subject comprises a human subject. In some embodiments, the sample comprises a blood sample or a tumor sample. In some embodiments, detecting comprises exposing the sample to an antibody and detecting the antibody binding to UCH-L3. In other embodiments, detecting comprises detecting the presence of an autoantibody to UCH-L3 (e.g., exposing the sample to an autoantibody specific antibody and detecting the autoantibody specific antibody binding to the antibody). In some embodiments, the method further comprises step c) providing a prognosis to the subject. In some embodiments, detecting cancer further comprises detecting a stage of the cancer. In some embodiments, detecting cancer further comprises detecting a sub-type of the cancer.

In other embodiments, the present invention provides a kit for detecting the presence of cancer in a subject, comprising a reagent capable of specifically detecting the presence of UCH-L3; and instructions for using the kit for detecting the presence of cancer in the subject. In some embodiments, the antibody is a UCH-L3 specific antibody. In other embodiments, the antibody is an antibody specific for an autoantibody to USCH-L3.

In yet other embodiments, the present invention provides a method for eliciting a cancer specific immune response, comprising providing an immunogenic composition comprising UCH-L3 tumor antigen; and a subject diagnosed with a cancer; and administering the immunogenic composition to the subject under conditions such that the subject generates an immune response to the cancer. In some embodiments, the immunogenic composition further comprises an immune enhancing cytokine. In some embodiments, the immune enhancing cytokine is expressed by a cell. In some embodiments, the immune response results in a detectable decrease in the presence of the cancer. In other embodiments, the immune response results in a measurable decrease in the level of the UCH-L3 tumor antigen. In still other embodiments, the immune response results in a measurable decrease in the level of autoantibodies to the UCH-L3 tumor antigen. In some embodiments, the cancer is colorectal cancer. In some embodiments, the subject is a human.

In still further embodiments, the present invention provides a method of treating cancer in a subject, comprising providing a subject; and a therapeutic composition comprising an antibody directed toward UCH-L3; and administering the therapeutic composition to the subject. In some embodiments, the cancer is colorectal cancer. In some embodiments, the antibody is attached to a cytotoxic agent (e.g., including, but not limited to, of chemotherapeutic agents, radioisotopes, cytosines, cytokines, and toxins). In certain embodiments, the cytotoxic agent is Ricin A chain.

In some preferred embodiments the caner markers of the present invention are detected in combination with other colon cancer markers to provide a more informative profile (See e.g., U.S. Pat. No. 6,448,041 and U.S. Patent Publication Nos. 20030073105, 20030008284, and 20020160382; each of which is herein incorporated by reference in its entirety).

DEFINITIONS

To facilitate an understanding of the present invention, a number of terms and phrases are defined below:

The term "epitope" as used herein refers to that portion of an antigen that makes contact with a particular antibody.

When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "tumor antigen" refers to an immunogenic epitope (e.g., protein) expressed by a tumor cell. The protein may be expressed by non tumor cells but be immunogenic only when expressed by a tumor cell. Alternatively, the protein may be expressed by tumor cells, but not normal cells.

As used herein, the term "autoantibody" refers to an antibody produced by a host (with or without immunization) and directed to a host antigen (e.g., a tumor antigen).

As used herein, the term "cancer vaccine" refers to a composition (e.g., a tumor antigen and a cytokine) that elicits a tumor-specific immune response. The response is elicited from the subject's own immune system by administering the cancer vaccine composition at a site (e.g., a site distant from the tumor). In preferred embodiments, the immune response results in the eradication of tumor cells everywhere in the body (e.g., both primary and metastatic tumor cells).

As used herein, the term "host" refers to any animal (e.g., a mammal), including, but not limited to, humans, non-human primates, rodents, and the like, that is to be the recipient of a particular treatment. Typically, the terms "host" and "patient" are used interchangeably herein in reference to a human subject.

As used herein, the term "immune-enhancing cytokine" refers to a cytokine that is capable of enhancing the immune response when the cytokine is generated in situ or is administered to a mammalian host. Immune enhancing cytokines include, but are not limited to, granulocyte-macrophage colony stimulating factor, interleukin-2, interleukin-3, interleukin-4, and interleukin-12.

As used herein, the term "subject suspected of having cancer" refers to a subject that presents one or more symptoms indicative of a cancer (e.g., a noticeable lump or mass). A subject suspected of having cancer may also have on or more risk factors. A subject suspected of having cancer has generally not been tested for cancer. However, a "subject suspected of having cancer" encompasses an individual who has received an initial diagnosis (e.g., a CT scan showing a mass) but for whom the sub-type or stage of cancer is not known. The term further includes people who once had cancer (e.g., an individual in remission).

As used herein, the term "subject at risk for cancer" refers to a subject with one or more risk factors for developing a specific cancer. Risk factors include, but are not limited to, genetic predisposition, environmental expose, preexisting non-cancer diseases, and lifestyle.

As used herein, the term "stage of cancer" refers to a numerical measurement of the level of advancement of a cancer. Criteria used to determine the stage of a cancer include, but are not limited to, the size of the tumor, whether the tumor has spread to other parts of the body and where the cancer has spread (e.g., within the same organ or region of the body or to another organ).

As used herein, the term "sub-type of cancer" refers to different types of cancer that effect the same organ (ductal cancer, lobular cancer, and inflammatory breast cancer are sub-types of breast cancer.

As used herein, the term "providing a prognosis" refers to providing information regarding the impact of the presence of cancer (e.g., as determined by the diagnostic methods of the present invention) on a subject's future health (e.g., expected morbidity or mortality).

As used herein, the term "detecting the presence of cancer in a subject" refers to detecting the presence of a tumor antigen or autoantibody indicative of cancer. In preferred embodiments, the detecting involves the diagnostic methods of the present invention.

As used herein, the term "cancer-specific immune response" refers to an immune response directed to a cancerous cell, or, in particular, a tumor antigen expressed by the cancerous cell.

As used herein, the term "subject diagnosed with a cancer" refers to a subject having cancerous cells. The cancer may be diagnosed using any suitable method, including but not limited to, the diagnostic methods of the present invention.

As used herein, the term "detectable decrease in the presence of said cancer" refers to a measurable decrease in diagnostic symptoms of a cancer (e.g., size of a tumor or lack of tumor antigen expression).

As used herein, the term "non-human animals" refers to all non-human animals. Such non-human animals include, but are not limited to, vertebrates such as rodents, non-human primates, ovines, bovines, ruminants, lagomorphs, porcines, caprines, equines, canines, felines, aves, etc.

As used herein, the term "gene targeting" refers to the alteration of genes through molecular biology techniques. Such gene targeting includes, but is not limited to, generation of mutant genes and knockout genes through recombination. When a gene is altered such that its product is no longer biologically active in a wild-type fashion, the mutation is referred to as a "loss-of-function" mutation. When a gene is altered such that a portion or the entirety of the gene is deleted or replaced, the mutation is referred to as a "knockout" mutation.

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses and modified viruses) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule including, but not limited to DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decreases production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element or the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, etc. (defined infra).

Transcriptional control signals in eukaryotes comprise "promoter" and "enhancer" elements. Promoters and enhancers consist of short arrays of DNA sequences that interact specifically with cellular proteins involved in transcription (T. Maniatis et al., Science 236:1237 [1987]). Promoter and enhancer elements have been isolated from a variety of eukaryotic sources including genes in yeast, insect and mammalian cells, and viruses (analogous control elements, i.e., promoters, are also found in prokaryote). The selection of a particular promoter and enhancer depends on what cell type is to be used to express the protein of interest. Some eukaryotic promoters and enhancers have a broad host range while others are functional in a limited subset of cell types (for review, See e.g., Voss et al., Trends Biochem. Sci., 11:287 [1986]; and T. Maniatis et al., supra). For example, the SV40 early gene enhancer is very active in a wide variety of cell types from many mammalian species and has been widely used for the expression of proteins in mammalian cells (Dijkema et al., EMBO J. 4:761 [1985]). Two other examples of promoter/enhancer elements active in a broad range of mammalian cell types are those from the human elongation factor 1α gene (Uetsuki et al., J. Biol. Chem., 264:5791 [1989]; Kim et al., Gene 91:217 [1990]; and Mizushima and Nagata, Nuc. Acids. Res., 18:5322 [1990]) and the long terminal repeats of the Rous sarcoma virus (Gorman et al., Proc. Natl. Acad. Sci. USA 79:6777 [1982]) and the human cytomegalovirus (Boshart et al., Cell 41:521 [1985]). Some promoter elements serve to direct gene expression in a tissue-specific manner.

As used herein, the term "promoter/enhancer" denotes a segment of DNA which contains sequences capable of providing both promoter and enhancer functions (i.e., the functions provided by a promoter element and an enhancer element, see above for a discussion of these functions). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques such as cloning and recombination) such that transcription of that gene is directed by the linked enhancer/promoter.

The presence of "splicing signals" on an expression vector often results in higher levels of expression of the recombinant transcript. Splicing signals mediate the removal of introns from the primary RNA transcript and consist of a splice donor and acceptor site (J. Sambrook et al., Molecular Cloning: A Laboratory Manual, 2nd ed., Cold Spring Harbor Laboratory Press, New York [1989], pp. 16.7-16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence that directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally at the 3' end of the coding region of a given gene in the genome. A heterologous poly A signal is one that is isolated from one gene and placed 3' of another gene. A commonly used heterologous poly A signal is the SV40 poly A signal. The SV40 poly A signal is contained on a 237 bp BamHI/BclI restriction fragment and directs both termination and polyadenylation (J. Sambrook, supra, at 16.6-16.7).

Eukaryotic expression vectors may also contain "viral replicons" or "viral origins of replication." Viral replicons are viral DNA sequences that allow for the extrachromosomal replication of a vector in a host cell expressing the appropriate replication factors. Vectors that contain either the SV40 or polyoma virus origin of replication replicate to high "copy number" (up to $10^4$ copies/cell) in cells that express the appropriate viral T antigen. Vectors that contain the replicons from bovine papillomavirus or Epstein-Barr virus replicate extrachromosomally at "low copy number" (~100 copies/cell).

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% G+C)$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$·H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$·H$_2$O and 1.85 g/l EDTA, pH adjusted to 7.4 with NaOH), 0.5% SDS, 5× Denhardt's reagent and 100 µg/ml denatured salmon sperm DNA followed by washing in a solution comprising 1.0× SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$·H$_2$O and 1.85 g/l EDTA, pH adjusted to 7.4 with NaOH), 0.1% SDS, 5× Denhardt's reagent [50× Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 [1972]). This amplification enzyme will not replicate other nucleic acid. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target". In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to the region of nucleic acid bounded by the primers. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

"Amino acid sequence" and terms such as "polypeptide" or "protein" are not meant to limit the amino acid sequence to the complete, native amino acid sequence associated with the recited protein molecule.

The term "native protein" as used herein to indicate that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "transgene" as used herein refers to a foreign gene that is placed into an organism by, for example, introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome-binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher (or greater) than that observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the mRNA-specific signal observed on Northern blots). The amount of mRNA present in the band corresponding in size to the correctly spliced transgene RNA is quantified; other minor species of RNA which hybridize to the transgene probe are not considered in the quantification of the expression of the transgenic mRNA.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "selectable marker" refers to the use of a gene that encodes an enzymatic activity that confers the ability to grow in medium lacking what would otherwise be an essential nutrient (e.g. the HIS3 gene in yeast cells); in addition, a selectable marker may confer resistance to an antibiotic or drug upon the cell in which the selectable marker is expressed. Selectable markers may be "dominant"; a dominant selectable marker encodes an enzymatic activity that can be detected in any eukaryotic cell line. Examples of dominant selectable markers include the bacterial aminoglycoside 3' phosphotransferase gene (also referred to as the neo gene) that confers resistance to the drug G418 in mammalian cells, the bacterial hygromycin G phosphotransferase (hyg) gene that confers resistance to the antibiotic hygromycin and the bacterial xanthine-guanine phosphoribosyl transferase gene (also referred to as the gpt gene) that confers the ability to grow in the presence of mycophenolic acid. Other selectable markers are not dominant in that there use must be in conjunction with a cell line that lacks the relevant enzyme activity. Examples of non-dominant selectable markers include the thymidine kinase (tk) gene that is used in conjunction with tk⁻ cell lines, the CAD gene, which is used in conjunction with CAD-deficient cells, and the mammalian hypoxanthine-guanine phosphoribosyl transferase (hprt) gene, which is used in conjunction with hprt-cell lines. A review of the use of selectable markers in mammalian cell lines is provided in Sambrook, J. et al., Molecular Cloning: A Laboratory Manual, 2nd ed., Cold Spring Harbor Laboratory Press, New York (1989) pp. 16.9-16.15.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The term "test compound" refers to any chemical entity, pharmaceutical, drug, and the like that is a candidate for use to treat or prevent a disease, illness, sickness, or disorder of bodily function. Test compounds comprise both known and potential therapeutic compounds. A test compound can be determined to be therapeutic by screening using the screening methods of the present invention.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

DETAILED DESCRIPTION OF THE INVENTION

The present invention relates to compositions and methods for cancer therapies and diagnostics, including but not limited to, cancer markers. In particular, the present invention provides tumor antigens associated with specific cancers and diagnostic assays for the detection of such antigens and associated autoantibodies as indicative of the presence of specific cancers (e.g., colorectal cancer).

In the United States, colorectal cancer is the second leading cause of all cancer deaths. In most cases colorectal cancer strikes men and women over age 50. If the cancer is found and treated early before it spreads to lymph nodes or other organs, the survival rate is higher. However, less than 40% of colon cancers are discovered at an early stage a time where interventions have a greater chance of success and where more options are available.

Age and health history can affect the risk of developing colon cancer. Risk factors include an age of 50 or older, a family history of cancer of the colon or rectum, a personal history of cancer of the colon, rectum, ovary, endometrium, or breast, a history of polyps (small noncancerous growths) in the colon, a history of ulcerative colitis (ulcers in the lining of the large intestine), and certain hereditary conditions, such as familial adenomatous polyposis and hereditary nonpolyposis colon cancer (HNPCC; Lynch Syndrome).

Colon cancer is diagnosed by fecal occult blood test, digital rectal examination, barium enema, or sigmoidocopy or colonoscopy. Treatment options and prognosis depend on the stage of the cancer (whether the cancer is in the inner lining of the colon only, involves the whole colon, or has spread to other places in the body) and the patient's general health. Treatment options include surgery (sometimes including colostomy), chemotherapy, and radiation.

The currently available diagnostic techniques are limited in their ability to decisively identify and characterize tumors. In view of the limitations of current cancer detection technologies, what are needed are tumor-specific markers that can be used to detect early stage colorectal cancers (e.g., tumors too small to be detected by conventional techniques) and can provide information about the morphology of the cancer. In addition, the art is in need of effective treatments for colorectal cancer.

The present invention thus provides improved diagnostic and treatment methods directed toward a specific cancer. The description below is divided into the following sections: I) identification of tumor antigens, II) antibodies, III) detection of tumor antigens, IV) cancer immunotherapy, V) other therapies and VI) transgenic animals.

I. Identification of Tumor Antigens

In some embodiments, the present invention provides a gel electrophoresis technique useful in the separation, identification, and characterization of tumor antigens. The technique is configured to identify antigens associated with a specific tumor type. Experiments conducted during the development of the present invention identified a series of tumor antigens specifically associated with cancer.

A. Separation and Identification Techniques

In some embodiments, proteins from non-cancerous and cancerous cells (and/or tissues) are separated using an established two-dimensional (2-D) PAGE procedure (See e.g., Strahler et al., 1989. Protein Structure: A practical approach, T. E. Creighton ed., IRL Press, England, pgs. 65-92). Briefly, cells and tissues are solubilized in lysis buffer containing carrier ampholytes. Proteins are then applied to isoelectric focusing gels and separated based on isoelectric point. The first-dimension gel is then loaded onto the second dimension gel (acrylamide gradient). Proteins are then transferred to a PVDF membrane for Western blotting or visualized by silver-staining of the acrylamide gradient gels. In some embodiments, proteins separated by 2-D PAGE are characterized using Western blotting. Following transfer to PVDF membranes, the membranes are incubated with serum obtained from patients or from controls and bound antibodies are visualized.

In some embodiments, proteins separated by 2-D PAGE are silver stained to visualize proteins. The proteins of interest are excised from the 2-D gels, purified, and digested with trypsin. Digested proteins are then analyzed using matrix assisted laser desorption ionization-time of flight (MALDI-TOF) mass spectroscopy. In preferred embodiments, proteins of particular interest are identified. In some embodiments, proteins are identified by using the search program MS-Fit (University of California, available at prospector.ucsf.edu) to search for proteins in the database NCBI.

In other embodiments, following 2-D separation, proteins are placed on protein microarrays. The microarrays are then probed with patient serum to identify autoantibodies. Protein microarrays may be generated using any suitable method including, but not limited to, those disclosed herein (See e.g., Experimental Section).

B. Identification of Autoantibodies

The 2-D analysis described above was used to identify proteins that elicited humoral immune responses in colorectal cancer patients but not normal patients (See Experimental section). In particular, UCH-L3 was identified. The detection of UCH-L3 finds utility in the diagnosis and characterization of colorectal cancer, as described below.

II. Antibodies

The present invention provides isolated antibodies. In preferred embodiments, the present invention provides monoclonal antibodies that specifically bind to an isolated polypeptide comprised of at least five amino acid residues of tumor antigens. In other embodiments, the present invention provides antibodies that recognize autoantibodies to the tumor antigens. These antibodies find use in the diagnostic and therapeutic methods described below.

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a tumor antigen or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against a tumor antigen or autoantibody of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide-activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a tumor antigen of the present invention (further including a gene having a nucleotide sequence partly altered) can be used as the immunogen. Further, fragments of the protein may be used. Fragments may be obtained by any methods including, but not limited to expressing a fragment of the gene, enzymatic processing of the protein, chemical synthesis, and the like.

III. Detection of Tumor Antigens

As described above, the presence of an immune response to specific proteins expressed in cancerous cells is indicative of the presence of cancer. Accordingly, in some embodiments, the present invention provides methods (e.g., diagnostic methods) for detecting the presence of tumor antigens. In some embodiments (e.g., where tumor antigens are expressed in cancerous cells but not non-cancerous cells), tumor antigen proteins are detected directly. In other embodiments (e.g., where the presence of an autoantibody in cancerous but not cancerous cells is indicative of the presence of cancer), autoantibodies to the tumor antigens are detected. In preferred embodiments, tumor antigens are detected directly in tumors or cells suspected of being cancerous.

The diagnostic methods of the present invention find utility in the diagnosis and characterization of cancers. For example, the presence of an autoantibody to a specific protein may be indicative of a cancer. In addition, certain autoantibodies may be indicative of a specific stage or sub-type of the same cancer.

The information obtained is used to determine prognosis and appropriate course of treatment. For example, it is contemplated that individuals with a specific autoantibody or stage of cancer may respond differently to a given treatment than individuals lacking the antibody. The information obtained from the diagnostic methods of the present invention thus provides for the personalization of diagnosis and treatment.

A. Detection of Antigens

In some embodiments, antibodies are used to detect tumor antigens in a biological sample from an individual. The biological sample can be a biological fluid, such as, but not limited to, blood, serum, plasma, interstitial fluid, urine, cerebrospinal fluid, and the like, containing cells. In preferred embodiments, the biological sample comprises cells suspected of being cancerous (e.g., cells obtained from a biopsy).

The biological samples can then be tested directly for the presence of tumor antigens using an appropriate strategy (e.g., ELISA or radioimmunoassay) and format (e.g., microwells, dipstick (e.g., as described in International Patent Publication WO 93/03367), etc). Alternatively, proteins in the sample can be size separated (e.g., by polyacrylamide gel electrophoresis (PAGE), in the presence or not of sodium dodecyl sulfate (SDS), and the presence of tumor antigens detected by immunoblotting (e.g., Western blotting). Immunoblotting techniques are generally more effective with antibodies generated against a peptide corresponding to an epitope of a protein, and hence, are particularly suited to the present invention.

Antibody binding is detected by techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

In some embodiments, an automated detection assay is utilized. Methods for the automation of immunoassays are well known in the art (See e.g., U.S. Pat. Nos. 5,885,530, 4,981,785, 6,159,750, and 5,358,691, each of which is herein incorporated by reference). In some embodiments, the analysis and presentation of results is also automated. For example, in some embodiments, software that generates a prognosis based on the presence or absence of a series of antigens is utilized.

B. Detection of Autoantibodies

In some embodiments, the presence of autoantibodies to a tumor antigen is detected. This approach to diagnosing and typing tumors is particularly suited to tumor antigens that are present, but not immunogenic, in normal cells and immunogenic in tumor cells. For example, in some embodiments, antibodies (e.g., monoclonal or polyclonal) are generated to the autoantibodies identified during the development of the present invention. Such antibodies are then used to detect the presence of autoantibodies using any suitable technique, including but not limited to, those described above.

In other embodiments, tumor proteins are attached to a solid surface. The presence of autoantibodies is identified by contacting the solid surface (e.g., microarray) with serum from the subject and detecting binding to a tumor marker. One exemplary method for performing such an assay is described in the experimental section below.

C. Detection Kits

The present invention further provides kits for the diagnosis and typing of cancer. In some embodiments, the kits contain antibodies specific for a tumor antigen or autoantibody, in addition to detection reagents and buffers. In preferred embodiments, the kits contain all of the components necessary to perform a detection assay, including all controls, directions for performing assays, and any necessary software for analysis and presentation of results.

D. Other Detection Methods

The present invention is not limited to the detection methods described above. Any suitable detection method that allows for the specific detection of cancerous cells may be utilized. For example, in some embodiments, the expression of RNA corresponding to a tumor antigen gene is detected by hybridization to an antisense oligonucleotide (e.g., those described below). In other embodiments, RNA expression is detected by hybridization assays such as Northern blots, RNase assays, reverse transcriptase PCR amplification, and the like.

In further embodiments of the present invention, the presence of particular sequences in the genome of a subject are detected. Such sequences include tumor antigen sequences associated with abnormal expression of tumor antigens (e.g., overexpression or expression at a physiological inappropriate time). These sequences include polymorphisms, including polymorphisms in the transcribed sequence (e.g., that effect tumor antigen processing and/or translation) and regulatory sequences such as promoters, enhances, repressors, and the like. These sequences may also include polymorphisms in genes or control sequences associated with factors that affect expression such as transcription factors, and the like. Any suitable method for detecting and/or identifying these sequences is within the scope of the present invention including, but not limited to, nucleic acid sequencing, hybridization assays (e.g., Southern blotting), single nucleotide polymorphism assays (See e.g., U.S. Pat. No. 5,994,069, herein incorporated by reference in its entirety), and the like.

Direct and/or indirect measures of tumor antigen expression may be used as a marker within the scope of the present invention. Because the present invention provides a link between tumor antigen expression and cancer, any indication of tumor expression may be used. For example, the expression, activation, or repression of factors involved in tumor antigen signaling or regulation may be used as surrogate measures of expression, so long as they are reliably correlated with tumor antigen expression and/or cancer.

E. Molecular Fingerprint

In some embodiments, the present invention provides "molecular fingerprints" of autoantibodies in cancer. For example, in some embodiments, protein microarrays allow the detection of a plurality of autoantibodies simultaneously. Such molecular fingerprints provide a profile of the presence of autoantibodies in particular cancers or cancer sub-types. The profiles find use in providing cancer diagnoses and prognoses. Such prognoses can be used to determine treatment course of action. For example, in some embodiments, the autoantibody profile of a particular cancer subtype is indicative of a cancer that is responsive to a particular choice of therapy. In other embodiments, autoantibody profiles are indicative of the aggressiveness of a particular cancer subtype and are used to determine the aggressiveness of treatment to be pursued.

IV. Immunotherapy

The tumor antigens identified during the development of the present invention find use in cancer immunotherapy. Such methods are improvements over the non-specific chemotherapeutic cancer therapies currently available. For example, in some embodiments, tumor antigens are used to generate therapeutic antibodies. In other embodiments, the tumor antigens of the present invention find use in the generation of cancer vaccines.

A. Pharmaceutical Compositions

In some embodiments, the present invention provides pharmaceutical compositions that may comprise all or portions of tumor antigen polynucleotide sequences, tumor antigen polypeptides, inhibitors or antagonists of tumor antigen bioactivity, including antibodies, alone or in combination with at least one other agent, such as a stabilizing compound, and may be administered in any sterile, biocompatible pharmaceutical carrier, including, but not limited to, saline, buffered saline, dextrose, and water. The pharmaceutical compositions find use as therapeutic agents and vaccines for the treatment of cancer.

The methods of the present invention find use in treating cancers as described in greater detail below. Antibodies can be administered to the patient intravenously in a pharmaceutically acceptable carrier such as physiological saline. Standard methods for intracellular delivery of antibodies can be used (e.g., delivery via liposome). Such methods are well known to those of ordinary skill in the art. The formulations of this invention are usefull for parenteral administration, such as intravenous, subcutaneous, intramuscular, and intraperitoneal.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, compositions (e.g., antibodies and vaccines) can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, compositions may be administered alone to individuals suffering from cancer.

Depending on the type of cancer being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of antibody or vaccine may be that amount that decreases the presence of cancerous cells (e.g., shrinks or eliminates a tumor or reduces the number of circulating cancer cells). Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For antibodies to a tumor antigen of the present invention, conditions indicated on the label may include treatment of conditions related to cancer.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts antibody levels.

A therapeutically effective dose refers to that amount of antibody that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference).

In some embodiments, the pharmaceutical compositions of the present invention further include one or more agents useful in the treatment of cancer. For example, in some embodiments, one or more antibodies or vaccines are combined with a chemotherapeutic agent. Chemotherapeutic agents are well known to those of skill in the art. Examples of such chemotherapeutics include alkylating agents, antibiotics, antimetabolitic agents, plant-derived agents, and hormones. Among the suitable alkylating agents are nitrogen mustards, such as cyclophosphamide, aziridines, alkyl alkone sulfonates, nitrosoureas, nonclassic alkylating agents, such as dacarbazine, and platinum compounds, such as carboplatin and cisplatin. Among the suitable antibiotic agents are dactinomycin, bleomycin, mitomycin C, plicamycin, and the anthracyclines, such as doxorubicin (also known as adriamycin) and mitoxantrone. Among the suitable antimetabolic agents are antifols, such as methotrexate, purine analogues, pyrimidine analogues, such as 5-fluorouracil (5-FU) and cytarabine, enzymes, such as the asparaginases, and synthetic agents, such as hydroxyurea. Among the suitable plant-derived agents are vinca alkaloids, such as vincristine and vinblastine, taxanes, epipodophyllotoxins, such as etoposide, and camptothecan. Among suitable hormones are steroids. Currently, the preferred drug is adriamycin. However, other suitable chemotherapeutic agents, including additional agents within the groups of agents identified above, may be readily determined by one of skill in the art depending upon the type of cancer being treated, the condition of the human or veterinary patient, and the like.

Suitable dosages for the selected chemotherapeutic agent are known to those of skill in the art. One of skill in the art can readily adjust the route of administration, the number of doses received, the timing of the doses, and the dosage amount, as needed. Such a dose, which may be readily adjusted depending upon the particular drug or agent selected, may be administered by any suitable route, including but not limited to, those described above. Doses may be repeated as needed.

B. Antibody Immunotherapy

In some embodiments, the present invention provides therapy for cancer comprising the administration of therapeutic antibodies (See e.g., U.S. Pat. Nos. 6,180,357; and 6,051,230; both of which are herein incorporated by reference).

In some embodiments, the therapeutic antibodies comprise an antibody generated against a tumor antigen of the present invention conjugated to a cytotoxic agent. Such antibodies are particularly suited for targeting tumor antigens expressed on tumor cells but not normal cells. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents will serve as useful agents for attachment to antibodies or growth factors, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention may include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some preferred embodiments, deglycosylated ricin A chain is utilized.

In any event, it is proposed that agents such as these may, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93:280 [1983]).

For example, in some embodiments the present invention provides immunotoxins targeted to tumor antigens of the present invention. Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In preferred embodiments, antibody based therapeutics are formulated as pharmaceutical compositions and described above. In preferred embodiments, administration of an antibody composition of the present invention results in a measurable decrease in cancer (e.g., decrease or elimination of tumor).

C. Cancer Vaccines

In some embodiments, the present invention provides cancer vaccines directed against a specific cancer. Cancer vaccines induce a systemic tumor-specific immune response. Such a response is capable of eradicating tumor cells anywhere in the body (e.g., metastatic tumor cells). Methods for generating tumor vaccines are well known in the art (See e.g., U.S. Pat. Nos. 5,994,523; 5,972,334; 5,904,920; 5,674,486; and 6,207,147; each of which is herein incorporated by reference).

In some embodiments, tumor vaccines are administered when cancer is first detected (e.g., concurrently with other therapeutics such as chemotherapy). In other embodiments, cancer vaccines are administered following treatment (e.g., surgical resection or chemotherapy) to prevent relapse or metastases. In yet other embodiments, cancer vaccines are administered prophylactically (e.g., to those at risk of a certain cancer).

In some embodiments, the cancer vaccines of the present invention comprise one or more tumor antigens in a pharmaceutical composition (e.g., those described above). In some embodiments, the tumor antigen is inactivated prior to administration. In other embodiments, the vaccine further comprises one or more additional therapeutic agents (e.g., cytokines or cytokine expressing cells).

In some embodiments (e.g., the method described in U.S. Pat. No. 5,674,486, herein incorporated by reference), selected cells from a patient, such as fibroblasts, obtained, for example, from a routine skin biopsy, are genetically modified to express one or more cytokines. Alternatively, patient cells that may normally serve as antigen presenting cells in the immune system such as macrophages, monocytes, and lymphocytes may also be genetically modified to express one or more cytokines. The cytokine expressing cells are then mixed with the patient's tumor antigens (e.g., a tumor antigen of the present invention), for example in the form of irradiated tumor cells, or alternatively in the form of purified natural or recombinant tumor antigen, and employed in immunizations, for example subcutaneously, to induce systemic anti-tumor immunity.

The vaccines of the present invention may be administered using any suitable method, including but not limited to, those described above. In preferred embodiments, administration of a cancer vaccine of the present invention results in elimination (e.g., decrease or elimination of tumors) or prevention of detectable cancer cells.

V. Other Therapies

The present invention is not limited to the therapeutic applications described above. Indeed, any therapeutic application that specifically targets tumor cells expressing the tumor antigens of the present invention are contemplated, including but not limited to, antisense therapies.

For example, in some embodiments, the present invention employs compositions comprising oligomeric antisense compounds, particularly oligonucleotides, for use in modulating the function of nucleic acid molecules encoding tumor antigens of the present invention, ultimately modulating the amount of tumor antigen produced. This is accomplished by providing antisense compounds that specifically hybridize with one or more nucleic acids encoding tumor antigens. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of tumor antigens. In the context of the present invention, "modulation" means either an increase (stimulation) or a decrease (inhibition) in the expression of a gene. For example, expression may be inhibited to potentially prevent tumor proliferation or stimulated to increase a cancer-specific immune response (e.g., as a cancer vaccine).

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a tumor antigen of the present invention. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular $—CH_2—$, $—NH—O—CH_2—$, $—CH_2—N(CH_3)—O—CH_2—$ [known as a methylene (methylimino) or MMI backbone], $—CH_2—O—N(CH_3)—CH_2—$, $—CH_2—N(CH_3)—N(CH_3)—CH_2—$, and $—O—N(CH_3)—CH_2—CH_2—$ [wherein the native phosphodiester backbone is represented as $—O—P—O—CH_2—$] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta 78:486 [1995]) i.e., an alkoxyalkoxy group. A further preferred modification includes 2'-dimethylaminooxyethoxy (i.e., a $O(CH_2)_2ON(CH_3)_2$ group), also known as 2'-DMAOE, as described in examples hereinbelow, and 2'-dimethylaminoethoxyethoxy (also known in the art as 2'-O-dimethylaminoethoxyethyl or 2'-DMAEOE), i.e., 2'-O—$CH_2$—O—$CH_2$—$N(CH_3)_2$.

Other preferred modifications include 2'-methoxy(2'-O—$CH_3$), 2'-aminopropoxy(2'-$OCH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2- aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2. degree ° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-S-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisensce oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption to generate pharmaceutical compositions as described above.

VI. Transgenic Animals Expressing Exogenous Genes and Variants Thereof

The present invention contemplates the generation of transgenic animals comprising an exogenous tumor antigen gene of the present invention or mutants and variants thereof (e.g., truncations). In preferred embodiments, the transgenic animal displays an altered phenotype (e.g., increased presence of tumor antigens) as compared to wild-type animals. Methods for analyzing the presence or absence of such phenotypes include but are not limited to, those disclosed herein. In some preferred embodiments, the transgenic animals further display an increased growth of tumors or increased evidence of cancer.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated. In other embodiments, transgenic and control animals are given immunotherapy (e.g., including but not limited to, the methods described above) and the effect on cancer symptoms is assessed.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

Experimental

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); ° C. (degrees Centigrade); and Sigma (Sigma Chemical Co., St. Louis, Mo.).

EXAMPLE 1

Detection of Autoantibodies to UCH-L3

This Example describes the detection of autoantibodies to UCH-L3 in the serum of patients with colon cancer.

A. Materials and Methods

Serum Samples

Following informed consent, sera were obtained at the time of diagnosis from 45 patients with colon cancer, 24 patients with lung cancer, 20 with inflammatory bowel disease, 15 with colon adenoma and from 15 healthy individuals.

Cell Lines and Cell Culture

The LoVo colon adenocarcinoma cell line was cultured (6% $CO_2$, 37° C.) in DMEM medium containing 10% fetal bovine serum, penicillin (100 units/ml), and streptomycin (100 units/ml), all purchased from Invitrogen. The cells were solubilized in lysis buffer (Wall et al., Analytical Chemistry 72, 1099-1111 [2000]) containing 6 M urea, 2 M thiourea, 1.0% n-octyl β-D-glucopyranoside, 2 mM dithioerythritol, protease inhibitor cocktail (Boehringer, Mannheim, Germany), and 2% ampholytes, pH 3.5-10 (Bio-Rad). The lysates were scraped, RNase A (10 U/ml) and DNase I (100 U/ml) were added, and the solution left on ice for 30 min. The supernatant was vortexed, clarified by centrifugation (20,000×g for 10 min), and collected.

Protein Fractionation

A preparative-scale Rotofor (Bio-Rad) was used to separate proteins in the first dimension (Madoz-Gurpide et al., Proteomics 1, 1279-1287 [2001]). Whole cell protein extracts were diluted to 55 ml with running buffer (the same buffer as the lysis buffer except that 0.5% n-octyl β-D-glucopyranoside was used), and separated by isoelectric focusing for 6 hr (10° C.). 20 separate fractions were collected. The protein concentration and pH of each fraction was measured as previously described (Madoz-Gurpide et al., 2001, supra).

The high-resolution liquid chromatography (HPLC) reversed phase column R2/H (Applied Biosystems) was used for the separation of proteins in the second dimension. Separations were performed at a flow rate of 1.3 ml/min using water/acetonitrile gradients (solvent A: 98% $H_2O$, 2% acetonitrile, 0.1% TFA; solvent B: 90% acetonitrile, 10% $H_2O$, 0.1% TFA). The gradient profile used was as follows: (0) 95% solvent A for 2.5 min; (1) 95 to 75% A in 2.5 min; (2) 75 to 35% A in 40 min; (3) 35% A for 5 min; (4) 35 to 15% A in 5 min; (5) 15 to 5% A in 5 min; (6) 5 to 95% in 5 min. Protein fractions were collected every 30 seconds (88 fractions from each 1D fraction) starting 10 min into the gradient, then immediately frozen at −80° C. The fractions were lyophilized under vacuum, and resuspended in 25 µl of 60% PBS, 40% glycerol.

Protein Microarrays 3968 features were prepared that consisted of 1760 distinct LoVo fractions in duplicate, 64 positive, and 384 negative controls, and arrayed onto nitrocellulose membranes supported on glass slides (Schleicher and Schuell) using a 32-pin Flexys arrayer, as previously described (Madoz-Gurpide et al., 2001, supra). Biotinylated BSA was printed to act as a "landmark" to orient the arrays.

Patient serum was analyzed with the microarrays. Each slide was placed in its hybridization chamber inside a GeneTAC Hybridization Station (Genomic Solutions). 100 µL serum was added at a 1:50 dilution in blocking solution (PBS containing 3% non-fat dry milk) as a source of primary antibody, and allowed to hybridize for 2 h at 22° C. under agitation. The microarrays were washed four times in PBST (PBS, 0.1% Tween-20) for 1 min, followed by another two 1 min-cycles of washing in PBS. Biotinylated anti-human IgG (Amersham) was introduced into the hybridization chamber at a dilution of 1:20 in blocking solution. Following a 1 hr incubation, the membranes were washed in PBST four times for 1 min, and twice in PBS for 1 min. Streptavidin, R-phycoerythrin (Molecular Probes, Eugene, Oreg.) was added at a dilution 1:100 for 20 min. The slides were washed four times in PBST for 1 min, two times in PBS for 1 min, and then centrifuged at 200×g to dryness. The microarrays were imaged at 550 nm using a GeneTAC LS-IV scanner (Genomic Solutions).

Analysis of Protein Microarray Images

Scanned microarrays were analyzed using the GeneTAC Biochip Analyzer software package (Genomic Solutions). Images were manually fitted with a grid and the spot intensities were measured. The local background was subtracted from the signal at each spot, and the resulting average intensity of each spot pixels determined. Spots and/or areas with obvious defects such as signal lower than background or high background were excluded from subsequent analysis.

Mathematical and Statistical Analysis of Antibody Reactivity

Variable signal brightness between slides was adjusted by subtracting from each average intensity value the $25^{th}$ percentile of the intensity measures in each patch (a rectangular area of dots printed by the same pin). Resulting intensity measures less than 10 were set to 10. Differences between batches of slides that were printed and hybridized as groups were observable in the data (4 batches), so the patch-adjusted intensity values were compared to the median of the values for normal samples, and dots were categorized as positively reacting if this relative reactivity was at least 2.0. Using this categorization, one-sided Chi-square tests comparing colon vs. normal and lung vs. normal were performed.

Protein Identification by Mass Spectrometry

2-D-RPLC fractions were solubilized (1:1 PBS and $NH_4HCO_3$), then subjected to trypsin digestion at 37° C. for 18 h. Protein identifications were performed by nano-flow capillary liquid chromatography coupled with electrospray quadrupole-time of flight tandem mass spectrometry (LC ESI Q-TOF MS/MS) using a Q-TOF Micro (Micromass, Manchester, UK). ESI MS/MS tandem spectra were recorded in the automated MS to MS/MS switching mode, with m/z-dependent set of collision offset values. Doubly and triply charged ions were selected and fragmented using argon as the collision gas. The acquired spectra were processed and searched against the non-redundant Swiss-Prot protein sequence database using ProteinLynx Global Server (available from Micromass).

High-Density Oligonucleotide Microarrays

High-density oligonucleotide microarrays (Affymetrix, Santa Clara, Calif.) were probed as previously described (Giordano et al., American Journal of Pathology 159, 1231-1238 [2001]). The arrays were scanned using the GeneArray scanner (Affymetrix). Image analysis was performed with GeneChip 4.0 software (Affymetrix). Expression values were calculated as previously described (Schwartz et al., Cancer Research 62, 4722-4729 [2002]).

2-D Polyacrylamide Gel Electrophoresis and Western Blotting

The procedure followed was as described previously (Strahler et al., 1989 Two-dimensional electrophoresis. In: Protein Structure. A Practical Approach., T. Creighton, ed. (England: IRL Press)). Proteins were run in the first dimension by IEF. For the second dimension separation, a gradient of 11-14% acrylamide (Crescent Chemical, Hauppauge, N.Y.) was used. Proteins were transferred to an Immobilon-P PVDF membrane (Millipore, Bedford, Mass.) or visualized by silver staining of the gels. The membranes were incubated with sera at a 1:200 dilution, and were then incubated with HRP-conjugated IgG antibodies (Amersham) at a dilution of 1:1000. Immunodetection was accomplished by ECL (Amersham). Patterns visualized were compared directly with Coomassie blue-stained blots from the same sample to determine correlation with protein patterns. An anti-UCH-L3 antibody (obtained from Dr. Keith Wilkinson, Emory University, Ga.) was used at a 1:10,000 dilution on Western blots in order to detect UCH-L3.

B. Results

Protein Microarray Based Assay for Autoantibodies in Sera from Patients with Colon Cancer Preparative quantities (approximately 500 mg) of solubilized proteins isolated from the LoVo colon adenocarcinoma cell line were resolved by Rotofor isoelectric focusing in the first dimension (Madoz-Gurpide et al., 2001, supra). Following a 6-hr isoelectric focusing separation period, 20 fractions covering the pI range of 3.5-10 were collected in polypropylene tubes by vacuum harvesting. Each Rotofor fraction was separated in the second dimension by reverse-phase liquid chromatography into 88 fractions, for a total of 1760 fractions. All fractions were lyophilized to dryness, resuspended in 25 µl PBS/glycerol, and then used to prepare protein microarrays. The volume of sample that every pin in the robot head can deliver is approximately 0.5 nL. Considering that the average concentration of total protein in each fraction was approximately 2.3 µg/µl and given that each reverse-phase fraction contained 1-10 proteins as identified by mass spectrometry, an estimation of the amount of individual proteins in each dot is approximately 200 pg with a wide range.

3698 features were arrayed on each slide, representing 1760 separate protein fractions in duplicate, from the LoVo colon adenocarcinoma cell line, as well as positive, negative, and landmark controls. Fifteen sera from colon cancer patients, 15 sera from lung cancer patients and 15 control sera from healthy subjects were individually hybridized to the LoVo protein microarrays. Scanned images were quantitatively analyzed for intensity of hybridization of spotted individual fractions with each serum. Control spots on the microarrays, including tetanus toxoid, human IgG, and biotinylated protein controls repeatedly showed similar reactivity in all sera assayed. A set of 39 of 1760 fractions showed greater reactivity with sera from colon cancer patients relative to healthy controls ($p<0.01$). Twenty four of 1760 fractions showed greater reactivity with sera from lung cancer patients relative to healthy controls ($p<0.01$). Only 5 fractions showed greater reactivity with sera from both colon and lung patients relative to healthy controls.

Identification of UCH-L3 Protein in Fraction L04428 by Mass Spectrometry

Among the 39 fractions that demonstrated greater reactivity with colon cancer sera, the most reactive fraction (L04428) exhibited reactivity with 9 out of 15 colon cancer sera. Given the distinctive pattern of reactivity of fraction L04428, a tryptic digest of the protein constituents of this fraction was prepared and subjected to identification by tandem mass spectrometry (ESI-Q-TOF). Analysis of fraction L04428 revealed that it contained the ubiquitin carboxyl-terminal hydrolase isozyme 3 (UCH-L3) protein. The precursor ion m/z 949.9609 resulting from the tryptic digest matched with a 16-aminoacid sequence of UCH-L3 against protein sequence database with good accuracy (error=0.09 Daltons).

High Level Expression of the UCH-L3 Gene and Protein in Colon Adenocarcinoma

To confirm the presence of UCH-L3 in fraction L04428, LoVo protein microarrays were probed with a rabbit anti-UCH-L3 antibody. Specific reactivity for fraction L04428 was found. The expression of UCH-L1 and L3 was further explored in different tumor types. UCH-L3 and L1 gene expression was analyzed in 329 tissue samples, consisting of 51 colon adenocarcinomas, 91 lung adenocarcinomas, 10 pancreatic tumors, 73 brain tumors and 104 ovarian tumors using DNA microarrays. UCH-L3 was found to be expressed at 3-5 fold higher levels in colon tumors than that observed in all other tumor types examined ($p<0.01$). In contrast, the UCH-L1 gene, whose protein product was found to be the target of autoantibodies in lung cancer (Brichory et al., 2001, supra), was highly expressed in lung cancer relative to colon cancer ($p<0.001$). Expression of these two genes was further examined in the LoVo colon adenocarcinoma and the A549 lung adenocarcinoma cell lines. The LoVo cell line expressed high levels of the UCH-L3 gene product, but did not express UCH-L1, whereas the A549 cell line expressed both the UCH-L1 and UCH-L3 gene products. The results obtained for UCH-L1 and UCH-L3 expression in tumors and cell lines using DNA microarrays were confirmed by real time PCR.

Validation of the Presence and Specificity of UCH-L3 Autoantibodies in Sera from Colon Cancer Patients by Western Blot Analysis The occurrence of autoantibodies to UCH-L3 in colon cancer and the specificity of the antibody response to UCH-L3 was examined by Western blot analysis of sera from patients with colon adenocarcinomas, inflammatory bowel disease, colon adenoma or lung cancer and of sera from healthy subjects. To this end, solubilized proteins from the LoVo cell line were resolved by 2-D PAGE and transferred onto Immobilon-P PVDF membranes. In order to identify the location of UCH-L3 by 2-D PAGE, the LoVo cell blots were hybridized with a rabbit anti-UCH-L3 antibody. A highly reactive protein spot was found with an estimated molecular weight of 26 kDa and with a pI of 4.7, concordant with the predicted mass and pI of UCH-L3. The protein was excised from silver-stained gels, subjected to tryptic digestion and identified as UCH-L3 by Q-TOF tandem mass spectrometry. 2-D Western blots of LoVo cell proteins were prepared and hybridized with different subject sera. Sera from 19/43 patients with colon cancer exhibited IgG-based reactivity against UCH-L3. In contrast, none of the sera from 15 healthy, 15 colon adenoma and 24 lung cancer sera were reactive with UCH-L3 (Table 1). Only 2/20 sera obtained from patients with inflammatory bowel disease exhibited immunoreactivity against UCH-L3. 13 colon cancer sera were analyzed by both protein microarray and by 2D Western blots. Ten of the 13 sera showed concordant results between the two methods. Taken together, autoantibodies to UCH-L3 protein exhibited a high degree of specificity to colon cancer.

TABLE 1

Anti-UCH-L3 IgG in patient sera.

| Serum | number of subjects | UCH-L3 autoantibody positive |
| --- | --- | --- |
| Normal | 15 | 0 |
| Adenoma patient | 15 | 0 |
| IBD patient | 20 | 2 |
| Colon cancer patient* | 43 | 19 |
| Lung cancer patient | 24 | 0 |

*Colon cancer samples were positive more frequently than the others (P = 0.0002 for a Fisher's exact test).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method for identifying subjects suspected of having colorectal cancer, comprising:
   a) providing a serum sample from a subject; and
   b) detecting the presence or absence of an autoantibody to ubiquitin carboxyl-terminal hydrolase isozyme 3 (UCH-L3) in said serum sample, wherein subjects having said a serum antibody to UCH-L3 are suspected of having colorectal cancer.

2. The method of claim 1, wherein said subject is a human subject.

* * * * *